(12) United States Patent
Curtis

(10) Patent No.: US 6,740,526 B1
(45) Date of Patent: May 25, 2004

(54) QUANTITATIVE TRANSIENT PROTEIN EXPRESSION IN PLANT TISSUE CULTURE

(76) Inventor: Wayne R. Curtis, 144 Creekside Dr., State College, PA (US) 16801

( * ) Notice: Subject to any disclaimer, the term of this patent is extended or adjusted under 35 U.S.C. 154(b) by 0 days.

(21) Appl. No.: 09/667,796

(22) Filed: Sep. 22, 2000

Related U.S. Application Data

(60) Provisional application No. 60/155,327, filed on Sep. 22, 1999.

(51) Int. Cl.[7] .......................... C12N 15/84; C12N 15/13; C12N 15/52; A01H 4/00
(52) U.S. Cl. ...................... 435/469; 435/69.1; 435/183; 435/252.2; 435/424; 435/425; 435/426; 435/429; 435/431; 800/288; 800/294
(58) Field of Search ........................... 435/172.3, 69.51, 435/468, 469, 412, 414, 415, 417, 419, 424, 425, 429, 431, 183, 69.1, 252.2, 426; 800/288, 294

(56) References Cited

U.S. PATENT DOCUMENTS

| | | | |
|---|---|---|---|
| 4,956,282 A | * 9/1990 | Goodman et al. | ........ 435/69.51 |
| 5,550,038 A | 8/1996 | Goodman et al. | |
| 5,591,616 A | * 1/1997 | Hiei et al. | ................ 435/172.3 |
| 6,300,545 B1 | * 10/2001 | Baszczynski et al. | ........ 800/294 |

FOREIGN PATENT DOCUMENTS

WO     WO 0011953     3/2000

OTHER PUBLICATIONS

Narasimhulu et al. The Plant Cell 8: 873–886 ( May 1996).*
Wongsamuth et al. Biotech. & Bioeng. 54(5): 401–415, Jun. 1997.*
Sastry et al. Plant Mol. Biol. Rep. 4(2): 93–7, 1986.*
Bakkeren et al. Cell 57: 847–857, Jun. 1989.*
Lorz et al., Gene transfer to cereal cells mediated by protoplast transformation, 1985, Mol. Gen. Genet., vol. 199, pp. 178–182.*
Lippincott et al., Cell walls of crown–gall tumors and embryonic plant tissues lack Agrobacterium adherence sites, 1978, SCIENCE, vol. 199, pp. 1075–1078.*
Stachel et al. "Identification of the signal molecules produced by wounded plant cells that activate T–DNA transfer in *Agrobacterium tumefaciens*" (1985) 318:624–629.
Quayle et al. "Characterization of a maize endosperm culture expressing zein genes and its use in transient transformation assays" Plant Cell Reports (1991) 9(10):544–548.
Rao and Flynn "GUS Protocols: using GUS gene as a reporter of gene expression: Microtiter plate–based assay for beta–D–glucuronidase: a quantitative approach" Gallagher ed. (1992) Part 2, No. 6, pp 89–99, Academic Press, San Diego, CA.
Singh et al. "Biotechnological Applications of Plant Cultures: Reactor design for plant cell suspension culture" Shargool et al. eds (1994) Chapter 8, pp. 151–184, CRC Press, Boca Raton, FL.
Singh et al. "Biotechnological Applications of Plant Culture: Reactor design for plant root culture"Shargool et al. eds. (1994) Chapter 9, pp. 185–206, CRC Press, Boca Raton, FL.
Su et al. "High density cultivation of *Anchusa oficinalis* in a stirred–tank bioreactor with in–situ filtration" Appl. Microbiol. Biotechnol. (1995) 44:293–299.
Ramakrishnan et al. "Elevated meristematic respiration in plant root cultures: implications to reactor design" J. Chem. Eng. Japan (1995) 28(4):491–493.
Rayon et al. "N–glycosylation of phytohemagglutinin expressed in bean cotyledons or in transgenic tobacco cells" Plant Physiol. Biochem. (1996) 34(2):273–281.
Gomord et al. "Recombinant proteins from Plants: Production of Foreign Proteins in Tobacco Cell Suspension Culture" Cunningham et al. eds. (1998) Chapter 12, pp 155–164, Humana Press; Towtowa, NJ.
Ramakrishnan et al. "Monitoring biomass in root culture systems" Biotechnology & Bioengineering (Mar. 1999) 62(6):711–721.
Hsiao et al. "Development of a low capital investment reactor system: Application for plant cell suspension culture" Biotechnology Progress (Jan. 1999) 15(1): 114–122.

* cited by examiner

Primary Examiner—David T. Fox
(74) Attorney, Agent, or Firm—McDermott, Will & Emery

(57) ABSTRACT

The subject invention is related to a method for recombinantly and transiently producing a polypeptide in a plant tissue, which includes providing a plant tissue sample in a bioreactor; adding to the plant tissue sample, a sample of Agrobacterium containing a nucleotide sequence encoding the polypeptide on the T-DNA, co-culturing the plant tissue sample with the Agrobacterium so that the nucleotide sequence is transferred to the plant, allowing the plant tissue to transiently express the polypeptide, and then separating the polypeptide from the mixture.

16 Claims, 9 Drawing Sheets

QUANTITATIVE TRANSIENT PROTEIN EXPRESSION IN PLANT TISSUE CULTURE

CONTINUING DATA

The present application claims the benefit of priority to U.S. Provisional Application No. 60/155,327, filed Sep. 22, 1999, which application is hereby incorporated herein by reference in its entirety.

BACKGROUND OF THE INVENTION

1. Field of the Invention

The present invention relates to the field of recombinant polypeptide production in plants. The present invention also relates to the production of large-scale amounts of the polypeptide by mixing together plant tissue and recombinant microorganisms under controlled conditions to produce large amounts of transiently expressed recombinant polypeptides.

1. Background

The development of plant cell and tissue culture as a technology that will permit rapid evaluation of heterologous gene expression in plants is highly desirable. It would further be advantageous to rigorously monitor, control and operate bioreactors for plant cell and tissue culture. These bioreactor operational principles are utilized to correlate performance of transient expression systems and test expression of polypeptides such as monoclonal antibodies (MAbs), human growth hormone (hGH), blood transport proteins, including human transferrin (hTR) and so on.

The present application is directed to plant cell and root culture as a platform for protein expression in transgenic plants. Pilot-scale production of plant biomass would be a tremendous asset for plant biotechnology companies, particularly those who are developing transgenic plants as a means of producing biochemicals. The conventional establishment and characterization of a stable transgenic plant line involve a long process that takes two or more years. This development time, however, is too long to fit effectively into pharmaceutical drug discovery programs and is also hindering development of other plant biotechnology efforts such as plant-based production of industrial enzymes and modified polymeric materials (such as polyisoprenes, polyhydroxyalkanoates, collagen, and spider silk). The development of bioreactor-based biomass production to provide a more rapid vehicle for the testing of transgenes expressed in plant tissue and delivery of material for characterization and testing would, thus, be highly advantageous.

Despite industrial efforts, conventional information at the pilot scale for plant cell culture is limited, and scale-up from small (less than 5 liters) to pilot scale (50–500 L) remains an art. At the pilot scale, details are usually absent and little more than a growth curve is presented.

The bioreactor requirements for transient gene expression offer an excellent opportunity to refine plant cell culture growth techniques and conduct a more rigorous evaluation of the scientific basis of these control and operational strategies. As will be described in more detail below, the process involves the growth of plant suspended cells or root tissue within a bioreactor. This tissue acts as the expression host for transient expression of a foreign gene upon DNA introduction, analogous with industrially accepted microbial and insect cell culture systems. The process involves the addition of a live bacterial or viral vector to transfer DNA containing the gene for the desired protein to the cultured plant tissues. The timing of addition in terms of culture growth rate, physiological state, biomass and nutrient levels are important factors to achieving transient gene expression at levels sufficient to permit protein recovery and purification. Systematic operational procedures are validated in terms of biomass growth, oxygen mass transfer/demand and nutrient consumption. Both cell suspension and root cultures, as well as non-cultured mixture of plant tissue, may be used.

Thus, there is a need in the art for a method to recombinantly produce polypeptide at the milligram level sufficient for protein characterization.

SUMMARY OF THE INVENTION

The present invention has met the hereinbefore described need.

The present application describes technology related to utilizing cultured plant tissues for the rapid expression of heterologous protein in sufficient quantities to permit isolation, characterization and/or purification. An aspect of the present invention is on transient protein expression in a time frame of several days after the introduction of DNA to the process and does not rely on stable chromosomal integration. Growth of plant tissue culture in pilot-scale bioreactor systems provides the capability of introducing the DNA to tissue that is of a precisely defined physiological state. In addition to controlling the environmental conditions of the reactor, the plant tissue can be genetically altered to provide unique protein processing capabilities.

The invention has particular utility in the area of discovery and development of therapeutic proteins in transgenic plants. Although there has been tremendous strides in transgenic plant development, establishing transgenic plants, which express heterologous protein, is still a very slow process in comparison to alternative protein production platforms such as bacteria, yeast and others. The method of the present application reduces the time frame of obtaining quantitative:amounts of protein from a minimum of several months to a few days. The significance of this timesaving is that it takes place in the critical stage where the decisions need to be made on the eventual production platform. This decision is particularly important for therapeutics due to the drug approval process. Using the inventive technology, time-critical comparisons to alternative production platforms (bacteria, yeast, mammalian culture cell, baculovirus and so on) can be made.

It is an object of the present invention to provide a method for recombinantly and transiently producing a polypeptide in a plant tissue, comprising:
  i) providing a plant tissue sample in a bioreactor;
  ii) adding a sample of an Agrobacterium containing a nucleotide sequence encoding the polypeptide to the plant tissue sample;
  iii) co-culturing the plant tissue sample with the Agrobacterium so that the nucleotide sequence is transferred to the plant;
  iv) allowing the plant tissue to transiently express the polypeptide; and
  v) separating the polypeptide from the mixture.

According to the invention, the process is directed to large-scale transient expression of a polypeptide of interest. The plant tissue sample may include a plant cell, algal cell suspension culture, or a root culture. The plant may be a dicot or a monocot. In the case of a dicot the plant may include, but is not limited to, tobacco, potato, bean and soybean. In the case of a monocot, the plant may include, but is not limited to, corn.

Further, according to the method of the invention, the Agrobacterium may be *Agrobacterium tumefaciens* or *Agrobacterium rhizogenes*. Preferably, the Agrobacterium may be an auxotroph that is deficient in its ability to metabolize amino acids, vitamins, and/or nucleic acid precursors. If it is deficient for example in amino acid metabolism, it is desirable that the amino acid be a low cost amino acid, and not present in the co-culture medium in sufficient amounts to facilitate auxotroph growth without supplementation.

In the method of the invention, the polypeptide of interest may be a protein such as an enzyme, antibody or a therapeutic protein. It may also be a biomaterial or a gene product which is being tested for function (transcriptional factor, signal molecule, receptor, etc.).

The method of the invention further includes monitoring and controlling the bioreactor environment. Some of the factors to be monitored and controlled include, but are not limited to, the pH, optical density, temperature, media nutrient levels, dissolved oxygen levels, and polypeptide expression levels. In a preferred embodiment, the pH may be controlled to about 4.9 to 6.1.

As a preferred embodiment, the Agrobacterium may be an auxotroph and be added to plant culture at about 7 to about 14 days of the plant culture. Alternatively, the Agrobacterium can be an auxotroph and can be added to plant culture at a biomass concentration of about 25 to about 35 g(dry weight)/liter. Also, as a preferred embodiment, the time length of reaction between the plant culture and the Agrobacterium may be about 1 to about 4 days.

The amount of polypeptide expected to be obtained from the method of the invention may be more than about 1 mg from about 10 to 1000 liter volume of cells. It is understood that transient expression conditions determined in volumes of about 50 ml to about 1 liter cells can be considered to be predictive of large scale production reaction conditions in about 10 to about 1,000 liter volume bioreactors. The ability to achieve growth of plant cell cultures in bioreactors to small-scale shake flask culture utilizing the control and operational strategies that are outlined in the examples that follow.

In an alternative embodiment to the invention, an Agrobacterium DNA transfer activator may be added to the mixture of plant culture and Agrobacterium culture. The activator may be acetosyringone, syringaldehyde or other phenolic compounds that interact with the Agrobacterium proteins which detect wounded plants.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given hereinbelow, and the accompanying drawings which are given by way of illustration only, and thus do not limit the present invention, and wherein.

DETAILED DESCRIPTION OF THE INVENTION

Figure 1:
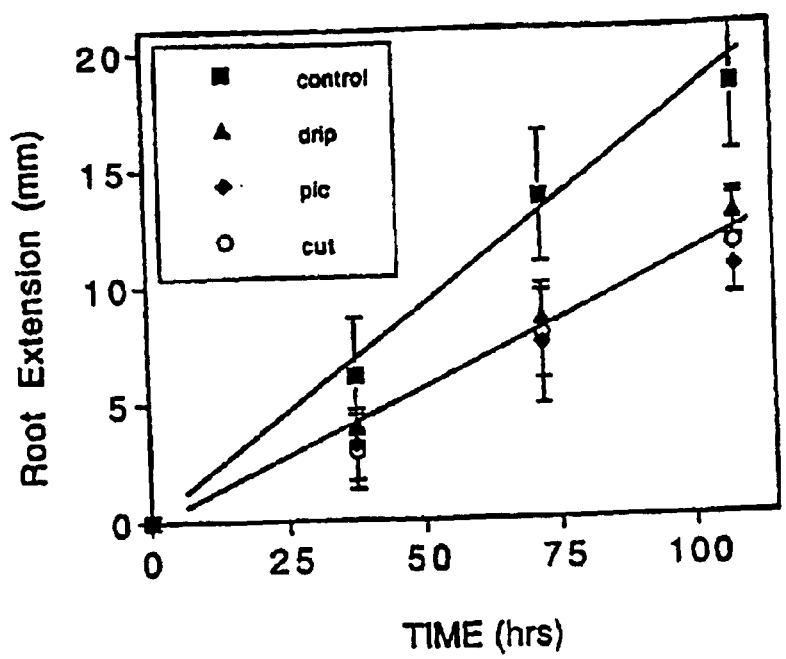
FIG. 1 shows growth of *Agrobacterium rhizogenes* transformed root cultures of *Nicotiana benthemiana* (N.b.) after exposure to tobacco mosaic virus. Growth rates assessed as extension rates of 1 cm root tips transferred to sterile plastic Petri dish containing solidified Gamborg B5 medium; extension measured daily by tracing roots through the bottom of the Petri dish for the following treatments: (cut) root growth on Petri dish, exposed to TMV by being cut with a scalpel dipped in axenic solution of 8.3 microg/mL TMV, (pic) root growth on Petri dish, rubbed with toothpick dipped in 8.3 microg/mL TMV distal to the site of excision several days prior to the tip excision, (drip) 50 microL of 8.3 microg/mL axenic TMV directly added to 50 mL of liquid suspension culture, (control) is root tips excised from N.b. cultures grown in 50 mL of B5 media in 125 mL milk shake flasks with 50 microL of sterile water added.

The invention is directed to achieving transient protein expression in plant tissue using Agrobacterium co-culture at a scale sufficient to carry out discovery, development and/or commercial production of proteins expressed in cultured plant tissues.

As used herein, the term "transient" means the expression of a recombinant polypeptide after DNA introduction without a requirement for selection of transformed transgenic cells where heterologous DNA is introduced into the plant chromosome.

As used herein, "large scale" production of polypeptides means production at a scale sufficient to permit purification for analytical purposes. In a large scale production of the polypeptide of interest, typically, about 10 L to over about 1000 L volume of cells is used, and about 1 mg or more of polypeptide is isolated and purified. More preferably, from a volume of about 100 L, about 100 mg amount of polypeptide is isolated. Even more preferably, from a volume of about 100 L, about 500 mg amount of the polypeptide is isolated. It is to be understood that the conditions determined in a volume of 50 ml to 1 liter is predictive of the factors and parameters that control the transient production of polypeptides in 10 to 1,000 liter (or higher) bioreactor vessels.

As used herein, a "bioreactor" may be any container in which a reaction between the plant and Agrobacterium may occur to produce transiently expressed polypeptides. Preferably, the container is about 50 ml to 10,000 liters in volume. More preferably, the volume is about 1 liter to 10,000 liters. Even more preferably, the volume is about 10 liters to 10,000 liters.(or higher) bioreactor vessels.

As used herein, a "bioreactor" may be any container in which a reaction between the plant and Agrobacterium may occur to produce transiently expressed polypeptides. Preferably, the container is about 50 ml to about 10,000 liters in volume. More preferably, the volume is about 1 liter to about 10,000 liters. Even more preferably, the volume is about 100 liters to about 1,000 liters.

The amount of plant or bacterial cells used depends on several factors which require monitoring. However, generally, about 10 g dry weight (DW)/L of plant tissue are used. Preferably, about 20 g DW/L or plant tissue are used. Even more preferably, about 40 g DW/L or plant tissue are used as determined by the bioreactor monitoring and control strategy.

As for the amount of bacterial cells, about $1 \times 10^4$ to about $5 \times 10^5$ cells/mL are added to the plant culture. Preferably, the amount of the bacteria is about $5 \times 10^4$ cells/mL. More preferably, the amount of bacteria is about $1 \times 10^4$ cells/mL.

The pH of the environment influences the transfer of DNA to plants for transient expression. Preferably, an effective pH is from about 4.9 to about 6.1 depending on the interaction with other parameters. More preferably, the pH is about 4.9 to about 5.2 with acetosyringone and about 5.8 to about 6.1 for syringaldehyde.

The length of time that the plant culture and the bacteria spend together so that the plant cell produces transiently expressed polypeptides, including proteins and enzymes, may be determined after monitoring the progression of the reaction. Such monitoring includes optical density, pH, temperature, media nutrient levels including dissolved oxygen, and protein expression levels as indicated by Western blot or ELISA. However, generally, the length of time of reaction is about 24 hours to about 4 days. Preferably, the length of time is about 3 days. More preferably, the length of time is about 2 days.

Just as the duration of reaction between the plant tissue and bacterial culture is a factor in the transient expression of the heterologous polypeptide, so is the time point in which the bacteria is added to the plant culture or mix. Although the time when the bacterial culture is added to the plant tissue can be varied depending on various monitoring conditions such as plant cell concentration, growth rate, nutrient levels, medium osmoticum, and/or medium calcium level, generally, a bacterial culture is added at about 7 to about 14 days of batch plant cell culture. More preferably, the point of addition of the bacterial culture is about 8 days of plant tissue culture. For higher tissue concentration culture, nutrients are added in a fed batch manner resulting in longer growth periods, in which case co-culture is initiated based on plant biomass not culture time. Plant tissue could also be produced in continuous culture to provided tissue at a constant physiological state.

As used herein, the term "auxotroph" means a culture of bacteria which cannot grow in the absence of a supplemental nutrient for which it does not have biosynthetic capacity to produce on its own. Preferably, the auxotroph lacks the ability to metabolize amino acids, vitamins such as thiamine and/or nucleic acid precursors such as purines and pyrimidines, since an organism can be multiply auxotrophic. More preferably, the auxotroph does not have the ability to metabolize a low cost amino acid such as leucine, and that amino acid is not found in the plant tissue medium either as a nutrient or due to leakage from the plant biomass.

It is understood that virtually any mutant or variation of the Agrobacterium may be used that may not necessarily be limited to auxotrophic mutants, so long as the trait is such that the Agrobacterium requires certain external source of nutrients or stimuli for it to continue to grow, and so long as the operator of the bioreactor can control the amount of such nutrient or stimuli to be added to the bioreactor.

The present invention is also directed to achieving enhanced transient protein expression in cell culture using direct plasmid delivery such as via calcium co-precipitated plasmid DNA.

The present invention is further directed to monitoring and controlling plant cell and tissue culture growth to provide precise optimal timing of transient expression. As a preferred embodiment, root culture is used as a platform for quantitative transient gene expression. In the monitoring process, factors such as mass-balance calculated nutrient levels and biomass fresh and dry weight based on media measurements of inorganics (e.g. conductivity), carbohydrate (e.g. refractive index) and tissue water content (via medium osmoticum) are considered. Environmental parameters such as temperature, pH and dissolved oxygen levels can also be monitored.

In a preferred embodiment, both root and cell suspension cultures are used to facilitate pilot scale production and purification of plant-expressed transgenic proteins in a bioreactor. Other forms of plant tissue culture such as shooty teratoma, embryo etc, are understood to act as plant host material for this transient expression methodology.

*Agrobacterium tumefaciens* is one of the primary vectors used in plant biotechnology for introducing foreign genes into plants. It has long been recognized that Agrobacterium can transfer genes from its tumor-inducing (TI) plasmid (or RI plasmid for A. rhizogenes) to the plant chromosome. The genes encoded on the DNA that is transferred (T-DNA) can be expressed transiently even if the DNA is not integrated into the plant chromosome. Alternatively, there are numerous other ways of introducing DNA into plant cells and protoplasts for transient expression including ballistics, polyethylene glycol (PEG) and electroporation. These transient expression techniques are used routinely to confirm that a specific DNA construct can be successfully expressed in a plant. Of these transient techniques, only ballistics along with Agrobacterium provide an efficient means of delivering the DNA across the cell wall. While these techniques are often used to achieve stable genetic transformation of plants, transient expression is still very useful for its ability to permit rapid protein expression. Agrobacterium can accomplish transient expression without the need to remove the plant cell wall, and has been used at the milliliter scale to obtain sufficient transient expression in cell suspension cultures to conduct preliminary characterizations, such as a Western blot. A scale of hundreds of liters may be used to produce greater quantities of recombinant polypeptides using this approach provided there is sufficient process control. A factor to achieving protein production at such a large scale is the utilization of monitoring, control and bioreactor technology. Agrobacterium containing the transgene of interest is added to the bioreactor at a prescribed biomass level and rate of growth as dictated by the bioreactor monitoring strategy. The plant cells and/or media will then be harvested several days after the infection to recover the transiently expressed protein.

Because plasmid DNA can be readily produced in a relatively inexpensive manner, direct plasmid delivery to cells is a useful way to achieve transient expression. In mammalian cells, this process is limited by nuclear transport, and in plants the cell wall is an additional barrier. Nuclear localization signals (NLS's) such as SV40 T-antigen consensus NLS (ScT) or more specifically, the M9-NLS complex with ScT will enhance direct plasmid expression in plant cells by facilitating DNA transport to the nucleus. In the Agrobacterium mediated T-DNA transfer, there are numerous NLS that surround the T-DNA to facilitate transport to the nucleus; therefore, there is no such need for heterologous NLS.

A factor to achieving pilot-scale implementation of an Agrobacterium-based transient expression is the timing of co-culture coupled with the concentration of plant tissue and bacterial cells utilized. Techniques of accurately predicting fresh and dry cell biomass based on mass balance techniques and simple off-line measurements of media conductivity (as a measure of inorganic nutrients), refractive index (as a measure of sugar concentration), and osmolarity (as an indicator of cellular water relations) are described in PCT/ US99/19662 (WO 00/11953), which reference is incorporated by reference herein in its entirety, particularly pages 20–30. The plant biomass is normally greatest at the end of a bioreactor run. While this favors expression in terms of available plant host tissue, growth is quite rapidly ceases with on onset of cell death to the depletion of nutrients. If there are too many nutrients at the time of Agrobacterium addition, the bacteria could overgrow and kill the plant cells or cause a strong detrimental defense response. Since the rate of growth and nutrient levels are necessarily coupled, it is expected that there may be a need for manipulating bacterial and/or plant cell culture through dynamically altering the media environment. Alternatively, an auxotrophic bacterial mutant may be made, which will be subject to growth control based on monitoring and controlling the level of certain nutrients in the mixture.

Root culture may have advantages over cell suspension cultures as a transient production system. An important advantage is that the root culture media is much cleaner due to the absence of cellular leakage found in plant suspension cultures. This simplifies isolation and purification of the recombinantly produced polypeptide. Another advantage of root culture is their superior genetic stability as compared to cell suspension cultures. This facilitates improvements to the root production platform using stable genetic transformation of the root culture. This permits modification of the plant host tissue both to enhance gene expression such as provision of replication functions in trans to the Agrobacterium vector, or modification of the protein chemistry such as altered post-translational modification such as glycosylation. Alternatively, the plant host tissue need not be a cultured sample. Rather, it is possible that field-harvested plant or algae biomass mixed with recombinant mutant bacteria will have the desired effect of large-scale plant production of the recombinant polypeptide.

In another embodiment, instead of delivering a simple DNA construct containing the transgene of interest, Agrobacterium can be used to deliver a self-replicating viral construct that contains the gene of interest to promote higher levels of gene expression than can be achieved by non-viral vectors. The ability to create TMV viral infection using a specially designed TMV cDNA with a ribozyme cleavage termination has been described by several researchers. There are also several descriptions of the use of genetically modified TMV viruses to express heterologous protein in intact plants. The effect of TMV in root culture is believed to be greater than in a plant suspension culture. First, the self-replicating and systemic spread of the virus would overcome the limitation of limited epidermal exposure. Secondly, roots have long been known to be a site of high levels of TMV during plant infection. Finally, the inventors have evidence that suggests that TMV infection and proliferation are possible in root cultures. The inventors established *Agrobacterium rhizogenes* transformed root cultures of *Nicotiana benthamiana,* which is highly susceptible to TMV. Upon exposure to TMV, there was a statistically significant reduction in cultured root extension rates, as would be expected during an infection where TMV ties up substantial biosynthetic capabilities within the cell (See FIG. 1). Transient protein expression also may be achieved using a genetically engineered TMV, either by simple virus addition or an Agro-infection vector containing TMV. Gemini viruses, which are DNA viruses, also may be used in the method of the invention. The ability to utilize viral replication functions in trans coupled with subgenomic viral replicons provides a means of reducing the vector size and overcoming whole-virus replicons which limit cell-to-cell viral movement.

Figure 2:
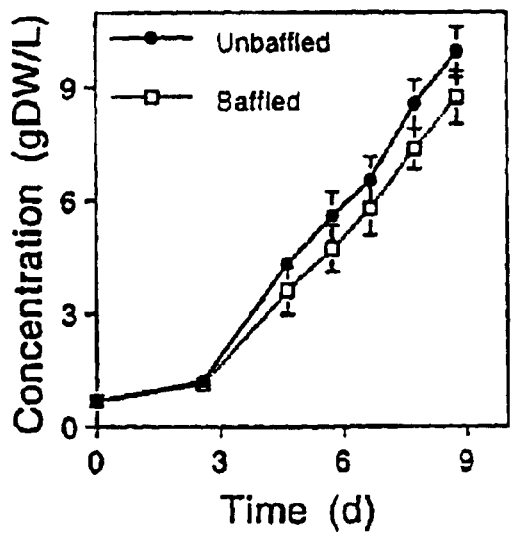
FIG. 2 shows a growth time course plot for root cultures of *Hyoscyamus muticus* grown in 125 mL Erlenmeyer flasks (120 rpm, 2.54 cm stroke) with and without baffles to assess the ability to grow under intensely agitated conditions. Roots were inoculated in 50 mL of B5 medium at a concentration of 1 g dry weight (DW) /L. Three replicates were used in the experiment. Refractive index was measured either two or three days apart by withdrawing a drop size liquid sample under sterile conditions. Refractive index was correlated to biomass concentration. Flasks were harvested after 9 days of culture.

Regarding the use of bioreactors, its operation involves a series of changes in gas composition and flow rate to achieve appropriate conditions for growth and production. For root cultures, numerous designs are possible. However, for simplicity, either a bubble column (as described for cells) or a more traditional stirred tank are preferred. This latter choice is based on the observation that root culture can be grown with traditional impeller agitation. FIG. 2 shows that roots grown in a baffled flask with intense agitation grow as fast as unbaffled flasks despite substantial physical disruption. Such mechanical damage may improve Agrobacterium transformation by increasing surface area and evoking the natural opportunistic response of Agrobacterium, which actively seeks out and infects wounded tissue. One of the most significant factors for pilot- to full-scale operation is the need to monitor the progress of culture growth. Due to the size of plant cells and cell aggregates, direct sampling of cell concentrations is problematic and for plant root culture, representative biomass sampling is not possible. Correlation of growth with nutrient depletion is a technique that can predict biomass accumulation without requiring accurate volumetric removal of biomass. Conductivity has been used as an indicator of inorganic consumption together with measuring media sugars consumption, which is the dominant organic carbon source. However, these correlative approaches lack the ability to account for concentration changes that result from water uptake into tissue or media addition. Since plant cell culture can be grown to occupy more than 40% of the physical reactor volume, water uptake can be very significant. Since the biomass volume ultimately determines the maximum possible cell concentration, this approach can be used to increase bioreactor productivity by increasing the dry cell concentration in the same fresh cell volume. Maintaining media osmoticum and low tissue water content has been successfully implemented using fed-batch of nutrients. By achieving high cell densities, the volumetric productivity (g/L/day) can be greatly increased (Su et al., High density cultivation of *Anchusa oficinalis* culture in a stirred-tank bioreactor with in-situ filtration. Appl. Microbiol. Biotechnol. 44:293–299, 1995). Use of fed-batch operation introduces substantial complexity to monitoring biomass growth: in addition to the added nutrients, the medium osmoticum changes which alters tissue water content and overall balance of water inside and outside the cells. An additional consideration for plant cell culture is that the long culture periods of one to several weeks results in substantial water loss due to evaporation. Since measurements such as conductivity can only provide estimates of the concentrations of nutrients in the media liquid volume, this approach is problematic for batch culture, and severely limited for fed-batch culture.

The method of the invention incorporates a water balance into an overall mass balance approach. The inventors demonstrated a correlation between medium osmotic pressure and tissue water content that permitted closing of the water balance once all media additions and losses (fed batch, sampling, evaporation) are measured (Ramakrishnan et al., Monitoring biomass in root culture systems. Biotechnology & Bioengineering 62:7111–721, 1999). This approach should be equally applicable to plant cell suspensions. This monitoring and control strategy was used to achieve plant cell biomass in excess of 38 g DW/L as the first run (7 L stirred tank bioreactor) of a newly established plant cell line (Ramakrishnan et al., Bioreactor design, operation and monitoring considerations for high density plant cell culture growth. Abstracts of papers, 213th National meeting of the American Chemical Society, AFDG paper no. 38. San Francisco, Calif. American Chemical Society, Washington, D.C., 1997). The utility of this monitoring and control strategy towards implementing an operational strategy for scale-up is described below in Example 7. This approach has been used to achieve extremely high volumetric productivity in a 150 L plant cell culture reactor. This operational strategy can reproduce the growth rates achieved in small scale shake flask culture, thereby facilitating the ability to scale up small scale shake flask transient expression studies to large scale operation.

The following examples are offered by way of illustration of the present invention, and not by way of limitation.

EXAMPLE 1

The data presented below result from the expression of the β-GUS (glucuronidase) reporter gene utilizing the specific construct of GUS that contains an interrupting eucaryotic intron in the sequence so that it cannot be expressed in the bacteria. As a result, the GUS enzyme activity is detected only after this intron is spliced out by the plant and expressed. The graphs in the figures are given in terms of relative activity where higher numbers represent higher levels of expression of the GUS gene after delivery of the DNA.

The graphs and data in this and subsequent examples show that the inventive process works with both plant root cultures and plant cell cultures. Transient expression using the GUS-Intron construct has been observed in all cultures tested thus far. In addition to the species in the examples, transient expression has been demonstrated in cell suspensions of *Solanum tuberosum* and *Hyoscyamus muticus* as well as root cultures of *Nicotiana benthemiana* and *Nicotiana tabacum*.

Figure 3:
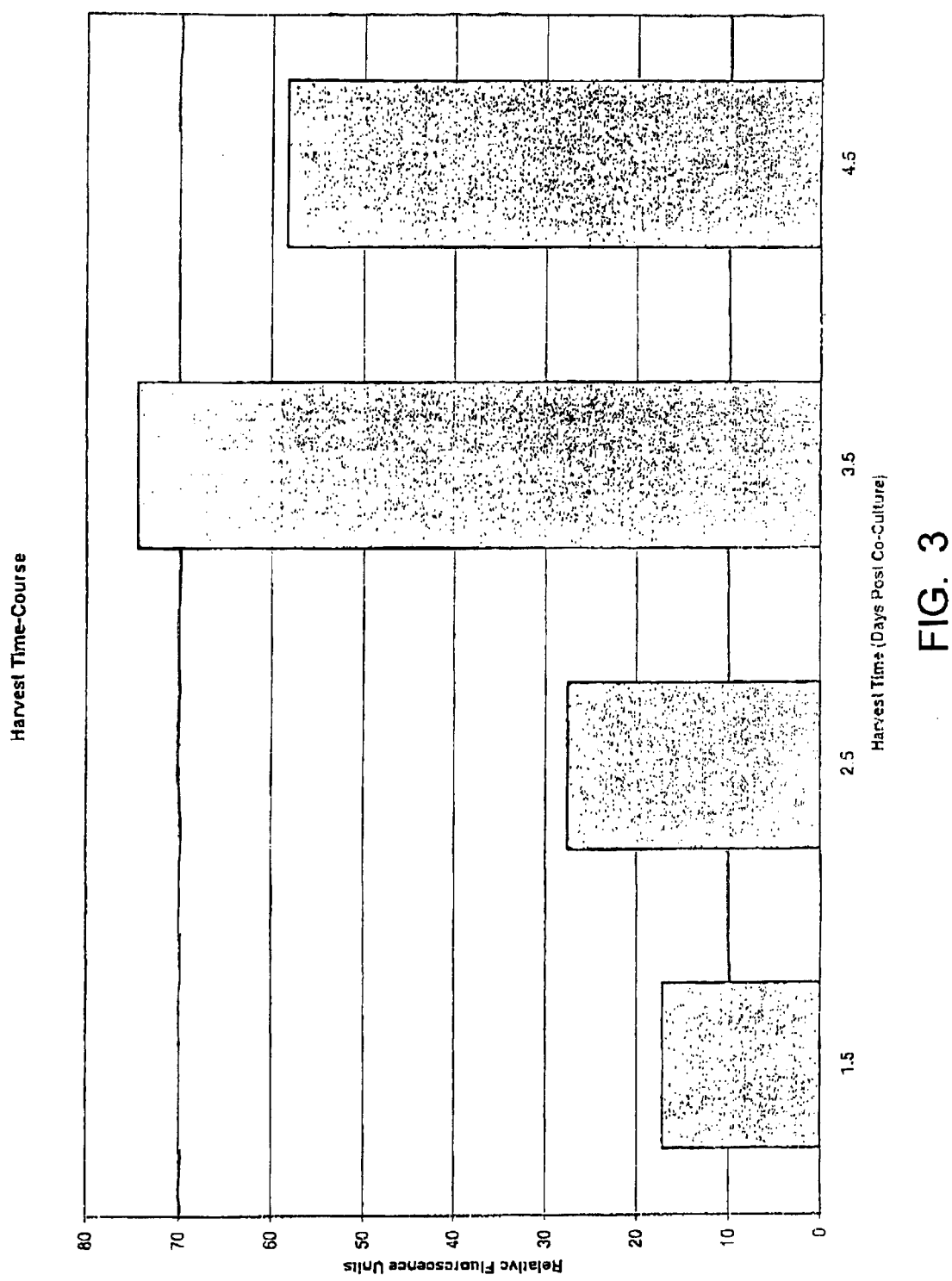
FIG. 3 shows the level of plant-expressed GUS ($\beta$-glucuronidase) at different times after the addition of the bacteria. Fourteen-day-old *Nicotiana glutinosa* NGA root culture was wounded in a lab blender (Waring model 34BL97-7012) for 10 seconds, prior to the introduction of *Agrobacterium tumefaciens* EHA105 containing the GUS-intron on a binary vector ,which is a non-auxotrophic C58 chromosomal background (EHA105::GUS-intron). The Agrobactcrium EHA105::GUS-intron suspension reached an OD) of approximately 0.75 at the time of infection. The initial bacterial titer in the NGA-bacteria mixture was 1% v/v. 100 microM acetosyringone was added to the co-culture media as a bacterial activator. The media was changed after approximately 15 hours of co-culture to minimize bacterial overgrowth of the culture. After about 1.5, 2.5, 3.5, and 4.5 days of co-culture, the NGA roots were harvested, frozen with liquid nitrogen, ground with a mortar and pestle and extracted with a cell lysis buffer. A cell extract aliquot was then analyzed for GUS activity by means of a fluorometric assay (Rao and Flynn, 1992. Microtiter plate-based assay for $\beta$-D-glucuronidase: a quantitative approach. In: GUS Protocols: using GUS gene as a reporter of gene expression, Academic Press, San Diego). A fluorogenic substrate, 4methylumbelliferyl-$\beta$-D-glucuronide (MUG), was added to the cell extract aliquot and fluorescence was read at excitation of 355 nm and emission of 460 nm. The intensity shown in the graph in FIG. 3 is relative to the light emission of a 100 nM MU (7 hydroxy -4-methylcoumarin) standard, whose intensity is set to be equal to 1000. MU is the product of the action of the GUS enzyme on the MUG substrate. All samples analyzed by the fluorometric GUS assay were diluted to a 0.1 $\mu g/\mu L$ concentration.

FIG. 3 shows the level of plantexpressed GUS at different times after the addition of bacteria. This shows that the length of time the host plant and the recombinant DNA bearing bacteria are co-cultured is an important factor in the level of expression of the polypeptide by the plant host cell.

Equally important is the time at which the bacteria is added into the plant culture, as can be determined depending on the results of monitoring plant cell culture conditions.

EXAMPLE 2

An auxotrophic system was developed to minimize or eliminate the problems of bacterial overgrowth in the presence of excess amount of nutrients in the plant media. Using a mutated form of Agrobacterium which is 'nutritionally impaired' provides control over the co-culture growth. A limiting factor for a non-auxotrophic methodology is that this approach is literally a purposeful contamination of an aseptic tissue culture run. Typical procedures for genetic transformation (and specifically as they apply to transient expression)virtually always involve a step of changing the media to reduce bacteria overgrowth. This last step is avoided (imperative for 1000 L scale work) by using an Agrobacterium auxotroph. These auxotrophs are created by mutagenesis. The auxotrophs in FIG. 4 were generated by randomly inserting DNA into the Agrobacterium chromosome using a TnS mutagenesis vector.

Figure 4:
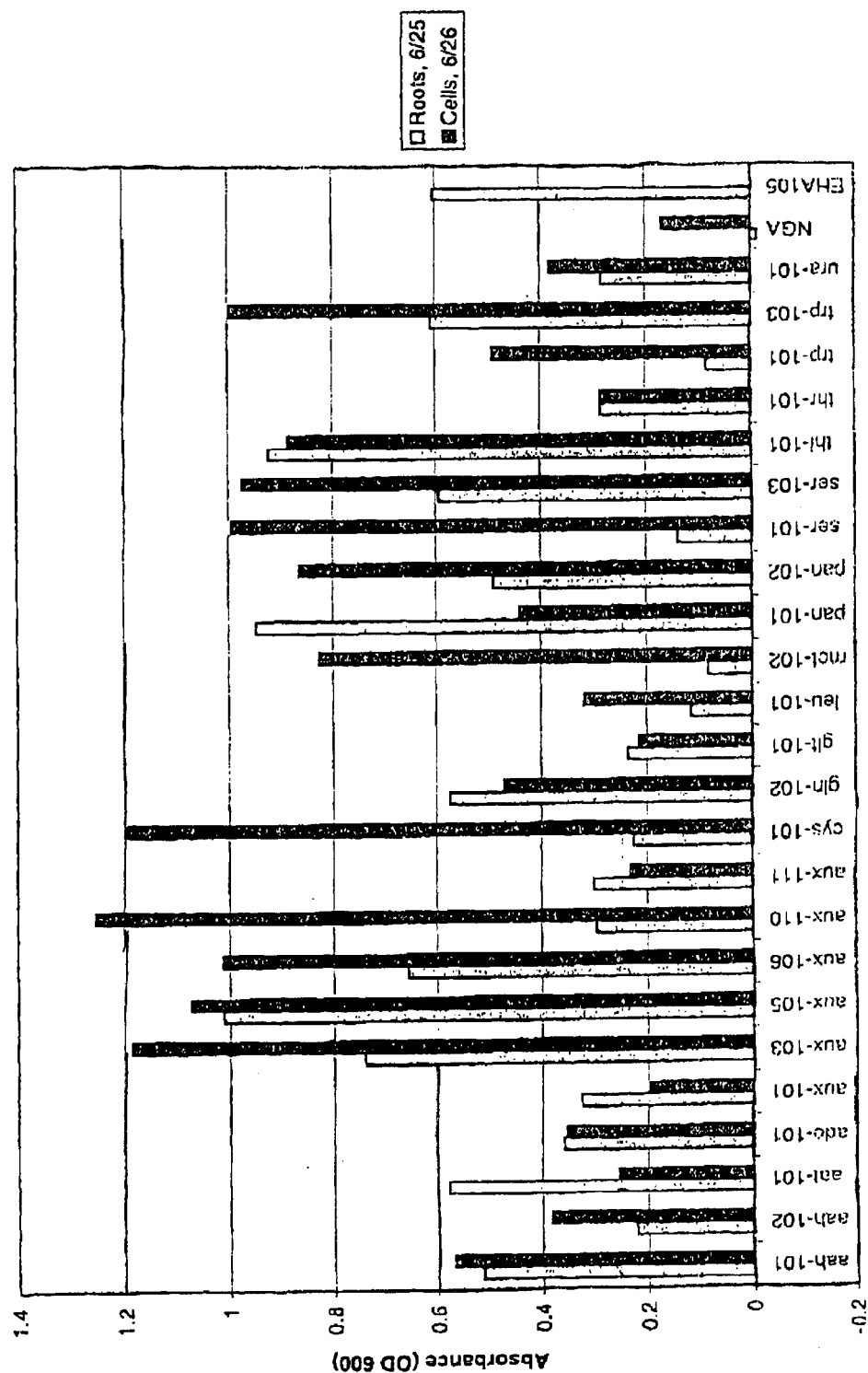
FIG. 4 shows a graph of the results of an Agrobacterium auxotroph screen for growth in the presence of roots or cells. Eight-day-old *Nicotiana glutinosa* NGA root culture or six-day-old BY2 cells were inoculated with *Agrobacterium tumefacienswhich* were C58 chromosomal background auxotrophs. The naming convention used is to designate the auxotrophs by their required supplement, where aux refers to an unknown requirement. *Agrobacterium tumefaciens* EHA105::GUS-intron was used as a control. The Agrobacterium suspensions reached an OD of approximately 1 at the time of infection. The initial bacterial titer in the NGA-bacteria mixture was approximately 10% v/v.

Auxotrophic Agrobacterium were added to cultures of actively growing *Nicotiana tabacum*BY2 cells and *Nicotiana glutinosa* roots. Subsequent growth of the bacteria was assessed after several days of co-culture using optical density(OD). FIG. 4 shows that (A) control of Agrobacterium growth in co-culture with plant tissues can be achieved, (B) this control is dependent on the auxotroph type, and (C) control is dependent on whether the coculture is with roots or cells. These variations in the ability to utilize auxotrophism to control bacterial overgrowth were expected due to variations in bacterial nutrient reserves and the leakage of nutrients from cells to the surrounding medium. As specific examples from this screen, the cysteine auxotroph is found to work well for roots, but not cells, the pantothenate auxotroph works well for cells but not roots, the glutamine/glutamate auxotroph achieves control for both roots and cells, whereas the thiamine auxotroph was not controlled in either root or cell culture.

EXAMPLE 3

Figure 5:
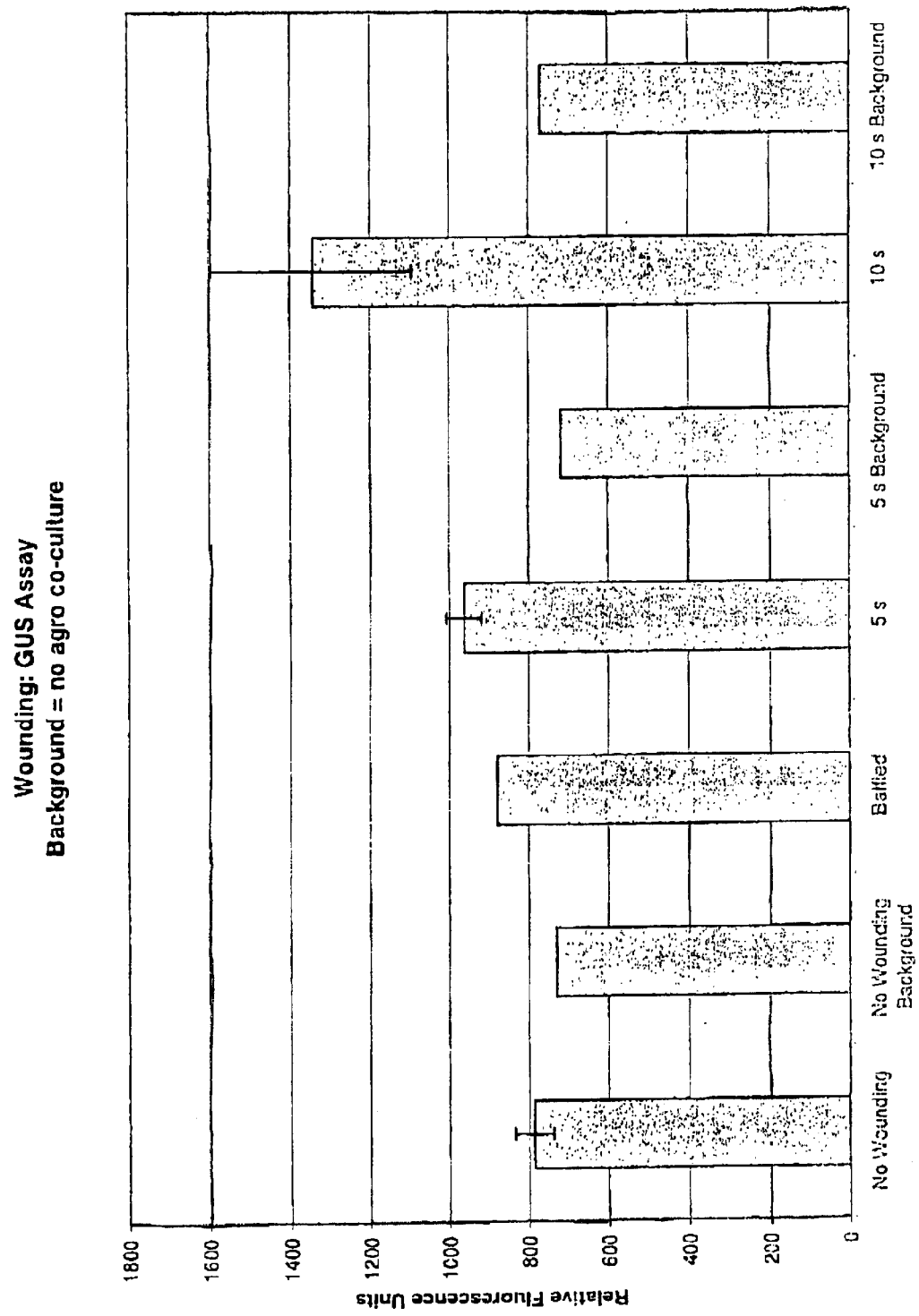
FIG. 5 shows a graph of the level of plant-expressed GUS in roots wounded for different periods of time. Nicotiana glutinosa (NGA )roots were wounded in a lab blender (Waring model 34BL97-7012) for about 0, 5, and 10 seconds prior to the introduction of *Agrobacterium tumefaciens* EHA105::GUS-intron, or were grown in a baffled flask and subjected to continuous wounding prior to Agrobacterium addition. The Agrobacterium EHA105::GUS-intron suspension reached an OD of approximately 0.75 at the time of infection. The initial bacterial titer in the NGA-bacteria mixture was 1% v/v based on a bacterial OD equal to 1. 100 microM acetosyringone was added to the co-culture media as a bacterial activator. The media was changed after approximately 14 hours of co-culture to minimize bacterial overgrowth of the culture. After 3 days of co-culture, the GUS assay was carried out as described for FIG. 3 above. For the 10 second wounding treatment, approximately 10 microg GUS/FW of tissue were produced based on calibration shown in FIG. 8 for GUS enzyme. For a nominal cell concentration of 300 g FW of cells/L this would correspond to a culture titer of 3 mg/liter.

The level of GUS expression depends upon the physical environment. The significance of this experiment is that the extent of tissue wounding (shear stress) can be controlled in a bioreactor system to optimize expression. The data show that different extent of wounding gives different expression levels. FIG. 5 shows a graph of plant-expressed GUS levels for roots wounded for different lengths of time.

Effect of Wounding on the Transient Expression of GUS

Figure 6:
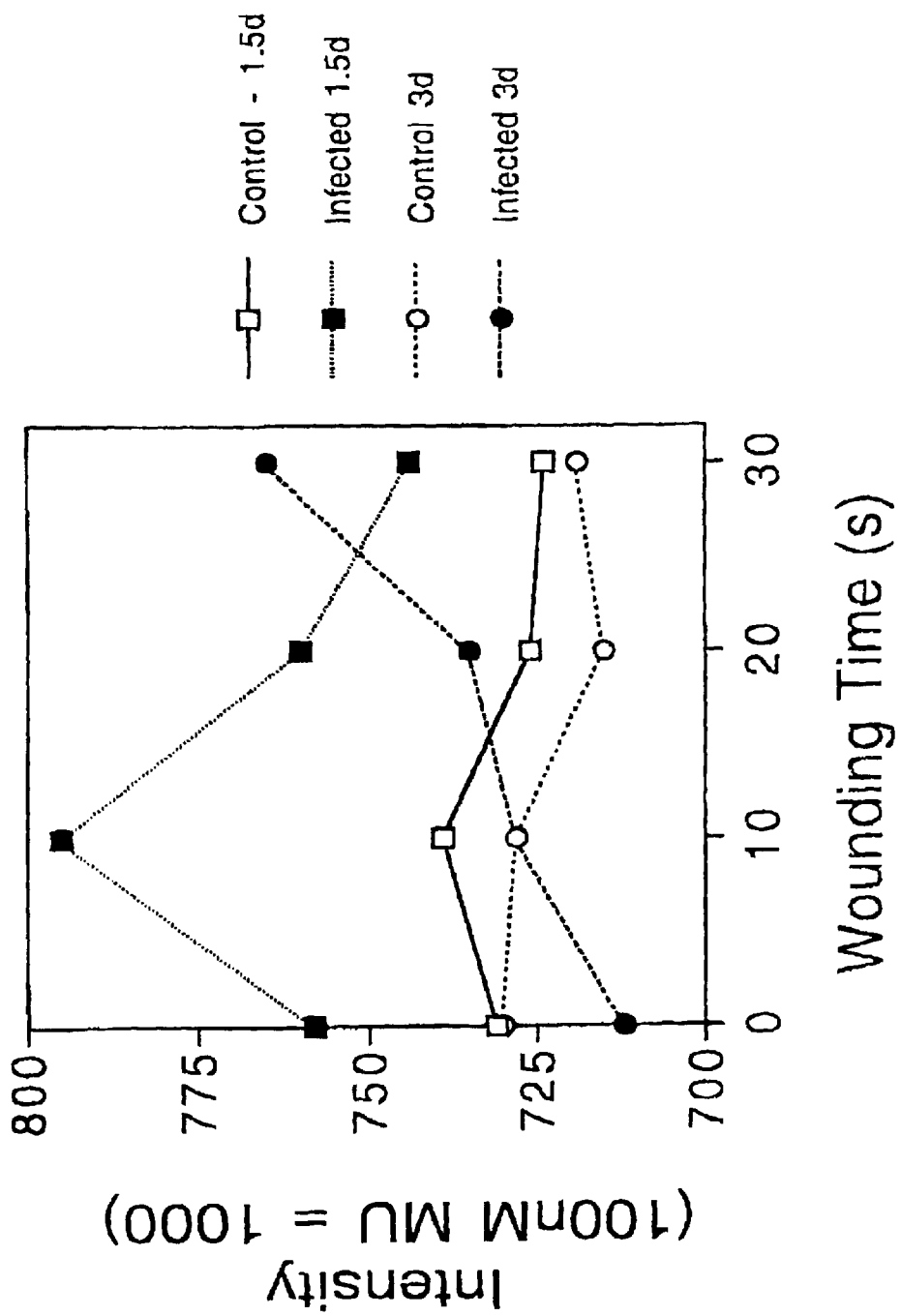
FIG. 6 shows a graph of the level of plant-expressed GUS in cells wounded for different periods of time. Nine-day-old Nicotiana tabacum (tobacco )BY2 cell suspension was wounded in a lab blender (Waring model 34BL97-7012) for 10, 20 and 30 seconds, prior to the introduction of *Agrobacterium tumefaciens* EHA105::GUS-intron. The Agrobacterium EHA105::GUS-intron suspension reached an OD of 1 at the time of infection. The initial bacterial titer in the BY2-bacteria mixture was 5% v/v. After 1.5 and 2.5 days of co-culture, the GUS assay was carried out as described for FIG. 3 above.

FIG. 6 shows that increasing the time cells are subjected to wounding cause them to increase the expression of GUS in a three day co-culture period.

Figure 7:
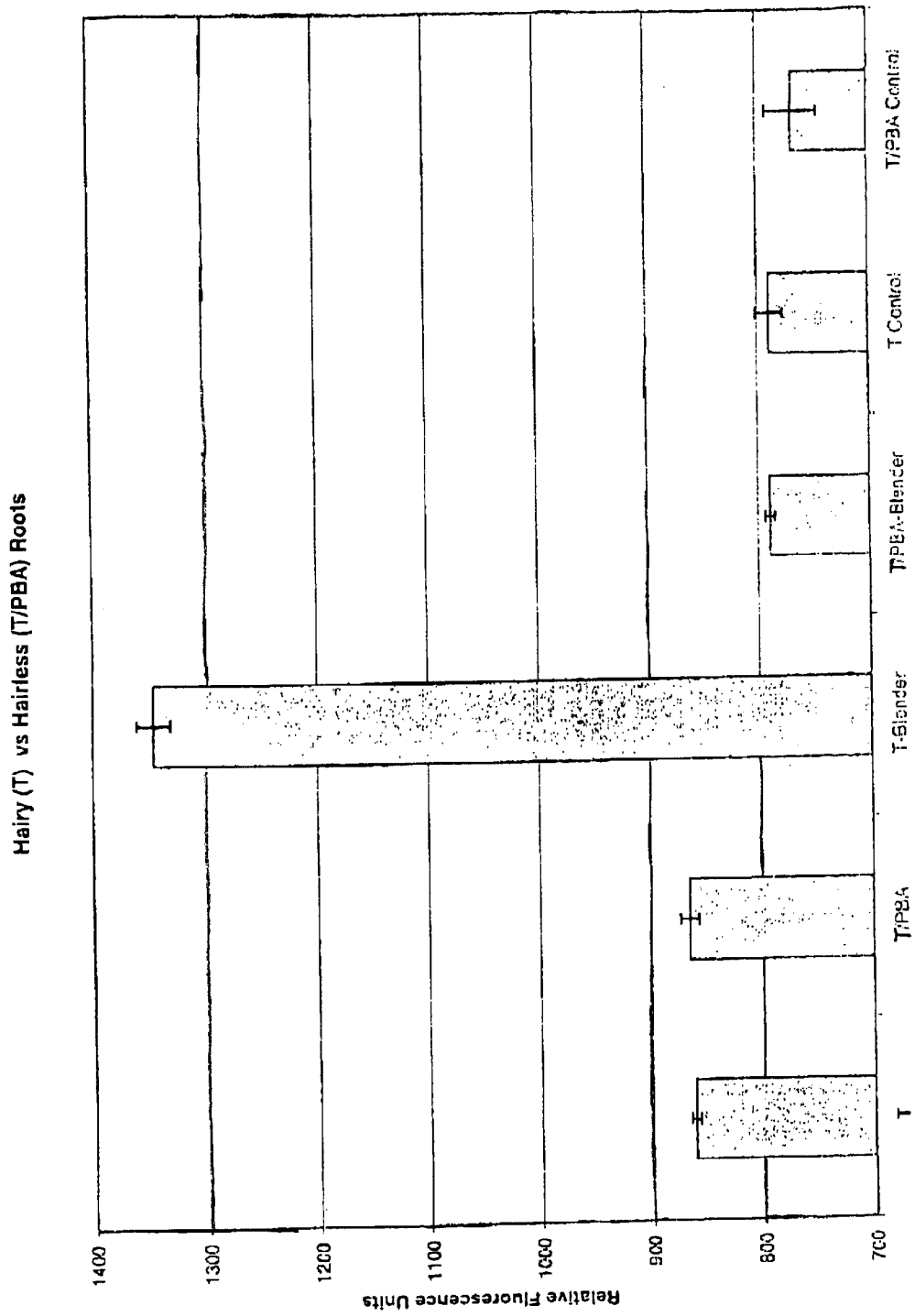
FIG. 7 shows the level of plant-expressed GUS in hairy and hairless roots. Twelve-day-old T-line hairy roots (T) and hairless roots (T/PBA), both *Hyoscyamus muticus*, were either wounded (T-Blender) or not wounded. The roots were wounded in a lab blender (Waring model 34BL97-7012) for 10 seconds prior to the introduction of *Agrobacterium tumefaciens* EHA105::GUS-intron. The Agrobacterium EHA105::GUS-intron suspension reached an OD of approximately 0.75 at the time of infection. The initial bacterial titer in the T or T/PBA-bacteria mixture was 1% v/v based on a bacterial OD equal to 1. 100microM acetosyringone was added to the co-culture media as a bacterial activator. The media was changed after approximately 15 hours of co-culture to minimize bacterial overgrowth of the culture. After 3 days of co-culture, the GUS assay was carried out as described for FIG. 3 above.

FIG. 7 shows a very interesting and novel twist to making this transient expression system work. The inventors developed a way of making *Hyoscyamus muticus* plant roots grow with or without root hairs based on the inventors adding a chemical to the media (pyrene butyric acid= PBA). When disrupted, the cell line with profuse root hairs has a much higher level of transient recombinant polypeptide expression. This could be due to the breaking off of the root hairs to help the bacteria colonize the plant surface and insert the DNA. At any rate, it shows that specific media manipulation (chemical environment) can be used in conjunction with physical environment to optimize expression.

EXAMPLE 4

Effect of pH on the transient expression of GUS by *Nicotiana tabacum*BY2 cell suspensions The process of transferring the DNA from the bacteria to the plant cell has been studied extensively because this is ultimately the basis of making genetically modified plants. As a result, there are a wide variety of parameters that are reported to affect the efficiency of DNA transfer. The significance of these results is that in bioreactor systems, control of pH and all the environmental conditions is easy to implement to optimize expression.

Figure 8:
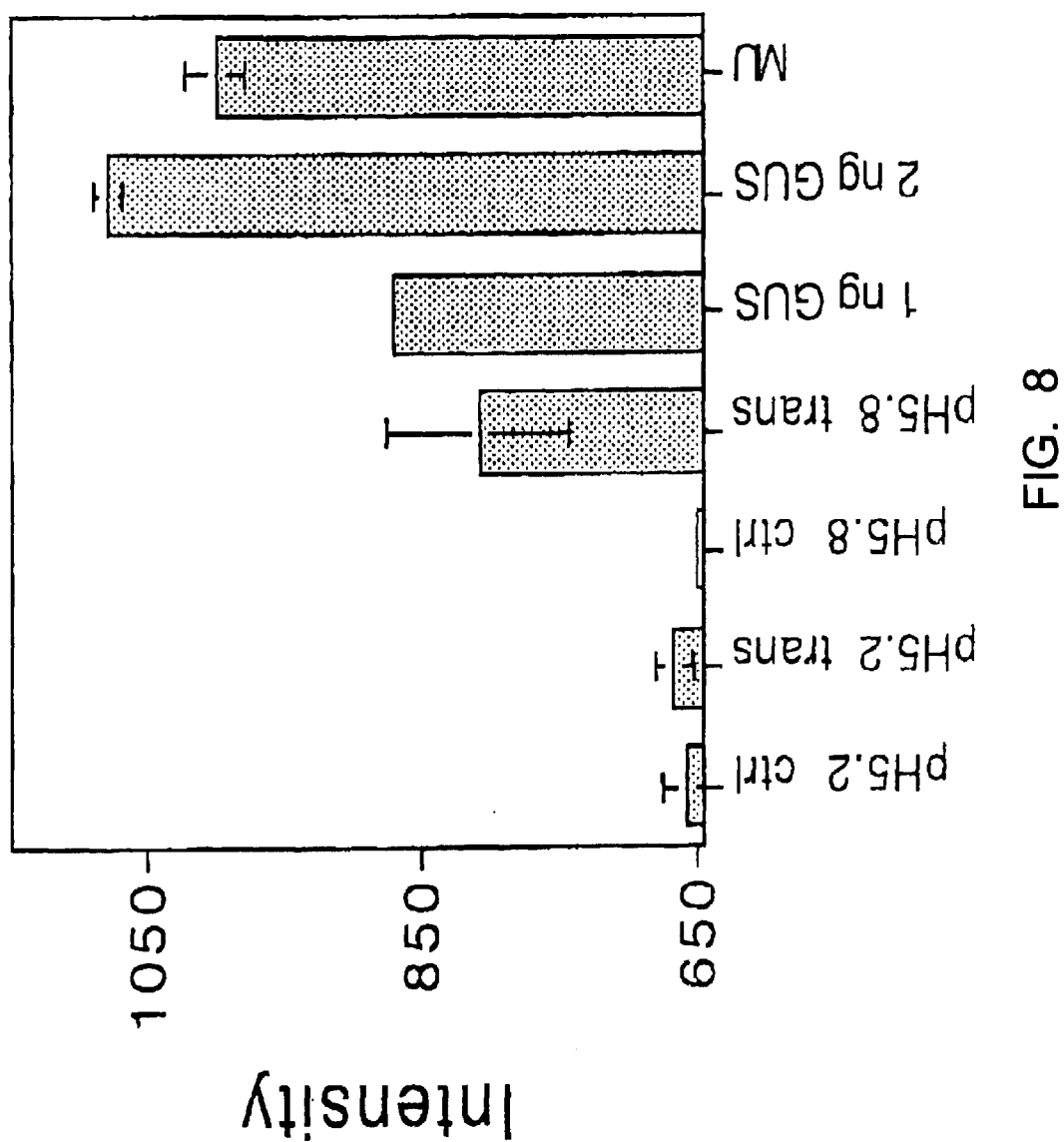
FIG. 8 shows the effect of pH of the surrounding medium on the expression of GUS by the plant cell suspensions. Tobacco BY2 cells were 5 days old. Cells were filtered and resuspended in MS medium, adjusted to pH 5.2 and 5.8. Agrobacterium EHA105::GUS-intron culture at an (optical density) OD=0.6 was added to the BY2 cell suspension at 5%v/v. GUS enzymes and MU product standards are shown in this figure which permit estimation of absolute expression level. Cells were harvested 3 days after the addition of bacteria to the cell suspension. GUS assay was carried out as described for FIG. 3 above. The fluorometric intensities corresponding to 1 nanogram (ng) GUS and 2 ng GUS were used to back calculate the amount of GUS produced during the co-culture. GUS produced by BY2 cells for the pH 5.8 treatment was 10 microg/FW tissue.

FIG. 8 shows that the pH of the surrounding medium has a large effect on expression. For these cell suspensions, a pH of 5.8 worked much better than pH 5.2

Precise interactions of chemical environment (and invariably chemical-physical) can be used to optimize the transient expression. The following example shows how the interaction of medium pH interacts with the activation process for DNA transfer from bacteria to plants.

EXAMPLE 5

The process of activation of the bacteria to enhance T-DNA transfer to plants happens in nature. Wounded plants produces phenolic compounds. When the bacteria senses these compounds, it responds as if there is a wounded plant nearby that is susceptible to infection and T-DNA transfer.

Figure 9:
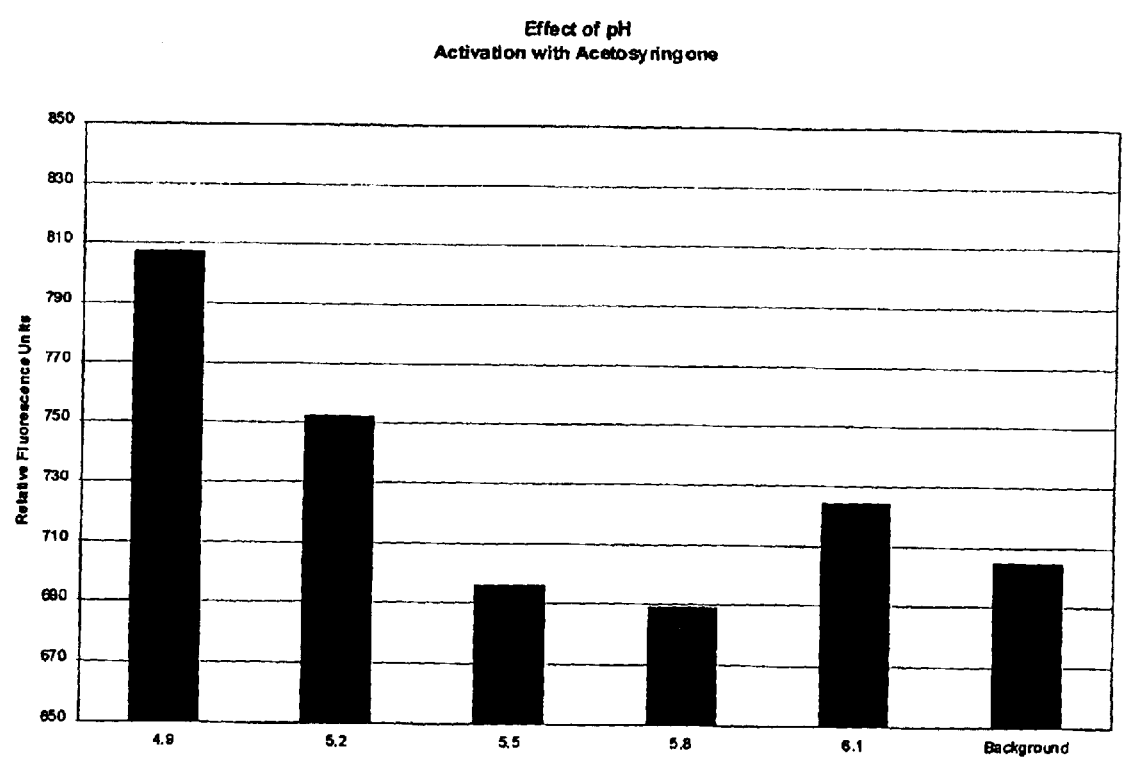
FIG. 9 shows the effect of pH together with activation by acetosyringone on the level of plant-expressed GUS. Nine-day-old *Nicotiana glutinosa* (NGA) roots were placed into fresh media adjusted to a pH of 4.9, 5.2, 5.5, 5.8, or 6.1, containing 100 microM acetosyringone. *Agrobacterium tumefaciens* EHA105::GUS-intron was added to the root culture after it had reached an OD of approximately 1 at the time of infection. The initial bacterial titer in the NGA-bacteria mixture was 1% v/v based on a bacterial OD equal to 1. The media was changed after approximately 17 hours of co-culture to minimize bacterial overgrowth of the culture. After 3 days of co-culture, the GUS assay was carried out as described for FIG. 3 above.
Figure 10:
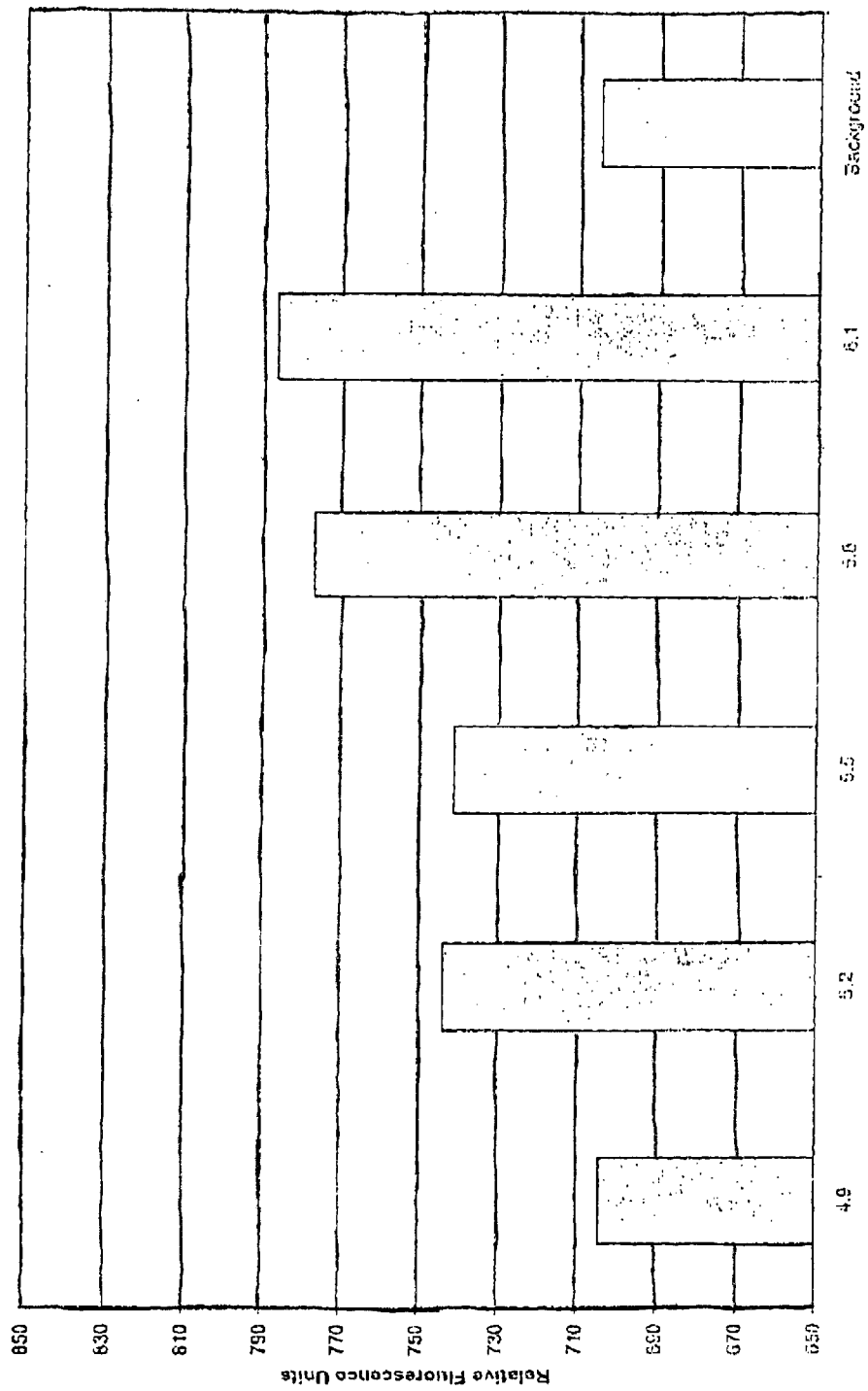
FIG. 10 shows the effect of pH together with activation with syringaldehyde on the level of plant-expressed GUS. Nine-day-old *Nicotiana glutinosa* NGA roots were placed into fresh media adjusted to a pH of about 4.9, 5.2, 5.5, 5.8, or 6.1, containing 100 microM syringaldehyde. *Agrobacterium tumefaciens* EHA105::GUS-intron background was added to the root culture. The Agrobacterium suspension reached an OD of approximately 1 at the time of infection. The initial bacterial titer in the NGA-bacteria mixture was 1% v/v based on a bacterial OD equal to 1. The media was changed after approximately 17 hours of co-culture to minimize bacterial overgrowth of the culture. After 3 days of co-culture, the GUS assay was carried out as described for FIG. 3 above.

In culture, compounds can be added to the media to simulate the wounded plant and make the bacteria prepare for DNA transfer. In FIG. 9, the addition of an activator (acetosyringone) is shown to be highly dependent upon the medium pH. Other phenolic/ plant wounding based activators, such as syringaldehyde also may be used, as demonstrated in FIG. 10. Once again, the significance of these observations is that these types of conditions, media additions and so on, are easily implemented in a large-scale bioreactor system to permit controlled and optimized production of the transient gene product.

EXAMPLE 6

Examples 6, 7, and 8 detail the characterization and bioreactor operation that can be used to implement the transient co-culture methodology. This example, details an extensive experimental design for plant cell culture characterization to provide the necessary kinetic and yield parameters to provide precise monitoring of the cell culture for the purpose of defining operational strategy for the plant cell culture (Example 7) and finally the optimal timing and conditions for Agrobacterium addition and co-culture (Example 8). Plant cell cultures are grown in50+ liter pilot scale bioreactors. The relatively large culture volume allows ample biomass and media component sampling while minimizing effects of wall growth and other anomalies of small-scale culture.

The following are measured at least daily as appropriate:
1) Inoculum initial fresh and dry cell concentrations, osmoticum, conductivity and refractive index.
2) Respiration rates as indicated by inlet and outlet gas composition ($CO_2$ and $O_2$/ $N_2$ inert).
3) Inlet and outlet humidity (for water balance/ evaporation calculations).
4) Medium properties: conductivity, osmotic pressure, pH, refractive index (RI) as well as nitrogen, phosphate, and sugar analysis as 'redundant' measurements for mass balance validation. Dissolved oxygen (DO) will be measured off-line by capturing medium in a glass syringe and injection of 1 mL into a microrespirometer (Ramakrishnan and Curtis, W. R. Elevated meristematic respiration in plant root cultures: implications to reactor design. Journal of Chemical Engineering of Japan 28(4):491–493,1995).
5) Biomass sample (volumetric sampling attempted)
6) Sample media volume, fresh and dry biomass.
7) Biomass elemental composition (C,H,N,O).
8) Any media feed volume and media properties (indicated in 1–4).
9) Final total fresh and dry biomass, total media volume and medium properties.

Simultaneous with these runs, shake-flask control experiments are run. A shake flask experiment involves roughly 30 uniformly inoculated flasks which provide time course data of all the necessary parameters including biomass, media and biomass composition, total biomass and media property measurements and unambiguous (whole flask) biomass concentrations.

In addition to typical dicot cultures such as tobacco, corn endosperm culture also may be used. Corn endosperm cultures are of particular interest because they may confer unique advantages as a development platform toward producing therapeutic proteins in transgenic corn kernels. Corn endosperm cultures display endosperm-specific metabolism such as zein and starch expression (Quayle et al., Characterization of a maize endosperm culture expressing zein genes and its use in transient transformation assays. Plant cell reports 9(10):544–548, 1991). Therefore, it may be possible to utilize the same DNA constructs that are optimized for corn expression (endosperm promoters, introns and monocot optimized codon usage).The data obtained from this study provides the necessary information to accurately predict the growth of plant tissues in a bioreactor based on simple media measurements as described previously. This information permits a systematic operation of the reactor to permit scale-up as described in Example 7.

EXAMPLE 7

The data obtained by the methods and principles set forth in Example 6 provide the data for implementing a precisely characterized plant tissue culture bioreactor run for the purpose of adding the Agrobacterium co-culture. The basic operational strategy is outlined for scales from 5 to 40 L in using a low-cost reactor system (Hsiao, T. Y.; Bacani, F. T.; Carvalho, E. B.; Curtis, W. R., "Development of a low capital investment reactor system: Application for plant cell suspension culture" , Biotechnology Progress, 15(1): 114–122, 1999.) where the control and operation of these reactors was accomplished without any internal bioreactor instrumenation and based solely on the media measurements previously described. These principles have been implemented to achieve scale-up in a 150 L bioreactor. The operational strategy is as follows:

Inoculate plant cell culture at roughly 4 g fresh weight (FW)/L or 0.22 g DW/L, which is substantially greater than the minimum inoculation and avoids extended lag phase. Plant root cultures have no minimum inoculation concentration and can be inoculated at any cell concentration.

Initiate a low gas flow rate to minimize volatile stripping, and cell floatation. (Larger tanks permit lower gas flow rates; a value of about 0.005 volumes of gas per volume of culture per minute (VYM) was used for the 150 L plant cell reactor.) Smaller vessels are constrained by the need to avoid sedimentation. An initial gas composition of about 40% $O_2$, about 5% $CO_2$(v:v) in air compensates for oxygen transfer at low gas flow rates; and $CO_2$can help to alleviate inoculation stress since it is an ethylene action inhibitor.

Cease oxygen and carbon dioxide supplementation when growth commences as indicated by media measurements of conductivity, refractive index and/or osmotic pressure. This indicates that the critical inoculation/ lagphase is over.

Increase gas flow rate to match the culture biological oxygen demand up to a gas flow of about 0.25 VVM. Further adjustments in oxygen availability in later stages of the culture will be accomplished with oxygen supplementation.

Implement a fed-batch of supplemental media to maintain conductivity (C) and refractive index (RI) greater than 0.4 millimho and 0.2 brix respectively to avoid kinetic limitations for nutrient uptake.

The principles set forth in Example 6 permit a precise calculation of the status of the culture in terms of plant tissue concentrations (fresh weight and dry weight) growth rate and biological oxygen demand. This approach to bioreactor operation has been used to scale to 150 L to produce over 53.8 kg fresh weight (1.5 kg dry weight) during a 33 day culture period using plant cell suspension of *Hyoscyamus muticus*. Additional information regarding bioreactors can be found in PCT/US99/19662 (WO 00/11953). This ability to systematically scale-up plant tissue culture permits systematic scale-up of the subsequent Agrobacterium coculture as described in Example 8.

EXAMPLE 8

Controlling the timing of product formation is important to achieve high titers of the product. Achieving optimum production is a balance of maximizing biomass, yet retaining sufficient energy and precursors to undertake substantial production. The issue of remaining nutrients is particularly important for the proposed use of a live bacterial vector that can also proliferate within the culture; however, a series of Agrobacterium auxotrophs have been created to minimize this problem. Co-culture of EHA105:GUS-intron early in the batch culture of the plant cells results in very low expression since the production of GUS is generally proportional to the biomass level. The plant biomass will normally be greatest at the end of a bioreactor run. While this favors expression in terms of available plant host tissue, plant culture nutrients are depleted, and the plant cells quickly die. The monitoring techniques described provide a means of precisely benchmarking the induction time for optimal production. Addition of Agrobacterium prior to nutrient exhaustion introduced the problem of bacterial overgrowth. Thus, auxotrophs with severely retarded growth in unsupplemented plant cell co-culture have been identified by using Tn5 mutagenesis. This could also be accomplished by crosses with existing auxotrophs generated by a variety of means including spontaneous or chemically induced mutants.

The following experiment is provided as an example of the further characterization that is carried out in a pilot-scale bioreactor to obtain the optimalco-culture conditions.

1) Inoculate the reactor and implement general operational strategy outlined in Example 7 above. . .
2) Starting at a level of roughly 50% consumption of sugar (mid-log phase as indicated by RI), remove approximately 300 mL of culture and divide into (3) 125 mL Erlenmeyer flasks.

Introduce the Agrobacterium vector containing a target polypeptide at three bacterial loadings. Agrobacterium is activated for about 24 hours with about 100 microM acetosyringone (Stachel et al., Identification of the signal molecules produced by wounded plant cells that activate T-DNA transfer in *Agrobacterium tumefaciens*. Nature 318:624–629, 1985) and inoculated at $10_7$, $10_8$ and $10_9$ bacteria/mL unless preliminary work indicates otherwise. Harvest cells at 24, 36, and 48 hours after vector introduction.

Assess target polypeptide expression using Western blot and ELISA.

Monitor free liquid bacterial cell counts utilizing a spiral dilution plater (Spiral Biotech).
4) Verify reproducibility with an independent run where induction is carried out in the entire reactor, with subsequent purification and characterization of the protein.

The 'induction' time course provides quantitative information on: the sensitivity of production to timing of vector addition, the optimal plant cell biomass to bacterial vector cell number, and the kinetics of product formation. The experimental space covers a wide range of induction conditions because it is difficult to predict what conditions will be most favorable for such a complex co-culture system which will not only vary by transgene construct and plant cell host, but we have observed several-fold variation for different cell lines of the same plant tissue culture. Plant cells display strikingly different morphologies in terms of degree of aggregation, cellular elongation, and shear sensitivity at different stages of batch culture (Singh and Curtis, Reactor design for plant cell suspension culture. In: Biotechnological Applications of Plant Culture, pp. 153–184 (Shargool, P. D.; Ngo, T. T., eds.) CRC Press, Boca Raton, Fla. 1994; Singh and Curtis, Reactor design for plant root culture. In: Biotechnological Applications of Plant Culture, pp. 185–206, (Shargool, P. D.; Ngo, T. T. eds.) CRC Press, Boca Raton, Fla. 1994). These factors contribute to large differences in cell wall properties and the susceptibility to Agrobacterium infection as a batch culture. Based on typical protocols for infection, infection efficiency favors rapidly growing mid-log cultures. The kinetic analysis provides quantitative information on rates and titer of the target polypeptide production. Although higher plant cell biomass loadings should favor higher productivities, the issues of phase of plant cell growth and interactions of plant-bacterium cell numbers may have a large influence on the outcome. Small-scale culture will assist greatly in focusing the range of parameters to be examined. Protein analysis such as gel electrophoresis/ELISA are routine.

After identifying optimal co-culture conditions, sufficient co-culture will be carried out at those conditions to permit recovery of the recombinant protein from the plant biomass and co-culture media using standard protein separation techniques including but not limited to ultrafiltration and chromatography.

All of the references cited herein are incorporated by reference in their entirety.

What is claimed is:

1. A method for transiently transforming plant cells or plant tissue for the large scale production of recombinant polypeptide comprising:
   i) providing a plant tissue sample to a bioreactor or cultivating plant cells or plant tissue in liquid medium in a bioreactor under conditions suitable for growth of the cells or tissue,
   ii) inoculating the plant cells or plant tissue with a culture of Agrobacteria when suitable growth of the cells or tissues is obtained, the Agrobacteria containing a vector comprising a nucleotide sequence encoding the recombinant polypeptide;
   iii) culturing the plant cells or plant tissue and the Agrobacterium under conditions suitable for transfer of the nucleotide sequence to the plant cells or the plant tissue to thereby produce transiently transformed plant cells or plant tissue,
   iv) growing the transiently transformed plant cells or plant tissue in liquid medium for about one to about four days under conditions that enable the transiently transformed plant cells or tissue to transiently express the recombinant polypeptide; and
   v) recovering the recombinant polypeptide from the transiently transformed cells or tissue of step (iv),
   wherein the conditions are monitored during step (i), (iii), and/or (iv) by measuring optical density, pH, temperature, nutrient levels, oxygen, conductivity, refractive index, osmolarity, calcium level of the medium, protein expression level, or a combination thereof; and
   wherein the Agrobacterium is an auxotroph deficient in its ability to metabolize amino acids, vitamins, and/or nucleic acid precursors, wherein said auxotroph has impaired ability to grow in a plant root or cell culture.
2. The method according to claim 1, wherein the bioreactor contains from about 50 ml to about 10,0000 liter of cells.

3. The method according to claim 1, wherein said plant tissue sample is a plant cell suspension culture.

4. The method according to claim 1, wherein said plant tissue sample comprise a root culture.

5. The method according to claim 1, wherein said Agrobacterium is *Agrobacterium tumefaciens* or *Agrobacterium rhizogenes*.

6. The method according to claim 1, wherein said plant is a dicot or a monocot.

7. The method according to claim 6, wherein said dicot is tobacco, potato, bean or soybean.

8. The method according to claim 6, wherein said monocot is corn.

9. The method according to claim 1, wherein the polypeptide is a protein.

10. The method according to claim 9, wherein said protein is an antibody or enzyme.

11. The method according to claim 1, wherein the Agrobacterium is added to plant culture at about 7 to about 14 days of the plant culture or at a plant biomass concentration of about 30 g DW/L.

12. The method according to claim 1, wherein the length of time for reaction between the plant culture and Agrobacterium is about 1 to about 4 days.

13. The method according to claim 1, wherein about 100 mg of the polypeptide is obtained from about a 100 liter volume of cells.

14. The method according to claim 1, comprising controlling the pH to about 4.9 to about 6.1.

15. The method according to claim 1, comprising adding an Agrobacterium DNA transfer activator to the mixture of plant culture and Agrobacterium culture.

16. The method according to claim 15, wherein the activator is acetosyringone or syringaldehyde.

* * * * *